(12) United States Patent
Cavett

(10) Patent No.: US 9,364,639 B2
(45) Date of Patent: Jun. 14, 2016

(54) MOVEABLE CUFF

(71) Applicant: Cook Medical Technologies LLC, Bloomington, IN (US)

(72) Inventor: Meridith Cavett, Dexter, MI (US)

(73) Assignee: Cook Medical Technologies LLC, Bloomington, IN (US)

( * ) Notice: Subject to any disclaimer, the term of this patent is extended or adjusted under 35 U.S.C. 154(b) by 172 days.

(21) Appl. No.: 14/203,691

(22) Filed: Mar. 11, 2014

(65) Prior Publication Data

US 2014/0276607 A1 Sep. 18, 2014

Related U.S. Application Data

(60) Provisional application No. 61/786,929, filed on Mar. 15, 2013.

(51) Int. Cl.
| | |
|---|---|
| *A61M 5/32* | (2006.01) |
| *A61M 25/04* | (2006.01) |
| *A61M 25/01* | (2006.01) |
| *A61M 25/06* | (2006.01) |
| *A61M 25/00* | (2006.01) |
| *A61M 25/02* | (2006.01) |
| *A61M 25/10* | (2013.01) |

(52) U.S. Cl.
CPC ............... *A61M 25/04* (2013.01); *A61M 25/01* (2013.01); *A61M 25/0194* (2013.01); *A61M 25/007* (2013.01); *A61M 25/0668* (2013.01); *A61M 2025/0031* (2013.01); *A61M 2025/0293* (2013.01); *A61M 2025/1075* (2013.01)

(58) Field of Classification Search
CPC .......... A61M 2025/024; A61M 25/04; A61M 2025/0293; A61M 25/0668; A61M 2039/0261
See application file for complete search history.

(56) References Cited

U.S. PATENT DOCUMENTS

| | | |
|---|---|---|
| 3,730,187 A | 5/1973 | Reynolds |
| 4,676,782 A | 6/1987 | Yamamoto et al. |
| 4,683,895 A | 8/1987 | Pohndorf |
| 4,955,890 A | 9/1990 | Yamamoto et al. |
| 5,236,422 A | 8/1993 | Eplett, Jr. |

(Continued)

FOREIGN PATENT DOCUMENTS

| | | |
|---|---|---|
| EP | 0 865 799 A2 | 9/1998 |
| EP | 1 475 123 B1 | 12/2008 |

(Continued)

OTHER PUBLICATIONS

JP 09-117503 English Language Translation May 6, 1997.

(Continued)

*Primary Examiner* — Emily Schmidt
(74) *Attorney, Agent, or Firm* — Woodard, Emhardt, Moriarty, McNett & Henry LLP

(57) ABSTRACT

Embodiments of the disclosed positioning systems can include a catheter assembly having a catheter with an external surface and an outer diameter, and a movable cuff assembly engaged around the circumference of the catheter. An exemplary movable cuff assembly includes a sleeve, a tissue ingrowth cuff affixed to the sleeve, and a clamp affixed to the sleeve, where when the first clamp is engaged, the movable cuff assembly is substantially fixed in position on the external surface of the catheter and wherein when the first clamp is disengaged, the movable cuff assembly is slidably movable over the external surface of the catheter.

18 Claims, 4 Drawing Sheets

(56) References Cited

U.S. PATENT DOCUMENTS

| | | |
|---|---|---|
| 5,509,902 A | 4/1996 | Raulerson |
| 5,599,311 A | 2/1997 | Raulerson |
| 6,358,230 B1 | 3/2002 | Davey |
| 6,719,781 B1 | 4/2004 | Kim |
| 6,939,328 B2 | 9/2005 | Raulerson |
| 7,258,685 B2 | 8/2007 | Kerr |
| 7,691,089 B2 | 4/2010 | Gresham |
| 7,753,889 B2 | 7/2010 | Rosenberg |
| 2004/0186461 A1 | 9/2004 | DiMatteo |
| 2004/0236314 A1 | 11/2004 | Saab |
| 2006/0079845 A1 | 4/2006 | Howard et al. |
| 2006/0135946 A1 | 6/2006 | Moehle et al. |
| 2007/0244490 A1 | 10/2007 | Moehle et al. |
| 2008/0009784 A1 | 1/2008 | Leedle et al. |
| 2008/0045894 A1 | 2/2008 | Perchik et al. |
| 2009/0292248 A1 | 11/2009 | Schon et al. |
| 2010/0049116 A1 | 2/2010 | Kerr |
| 2010/0174240 A1 | 7/2010 | Wells et al. |
| 2010/0241084 A1 | 9/2010 | Rosenberg |

FOREIGN PATENT DOCUMENTS

| | | |
|---|---|---|
| GB | 2 223 682 A | 4/1990 |
| JP | 08-024344 | 1/1996 |
| JP | 09-117503 | 5/1997 |

OTHER PUBLICATIONS

JP 08-024344 English Language Translation Jan. 30, 1996.

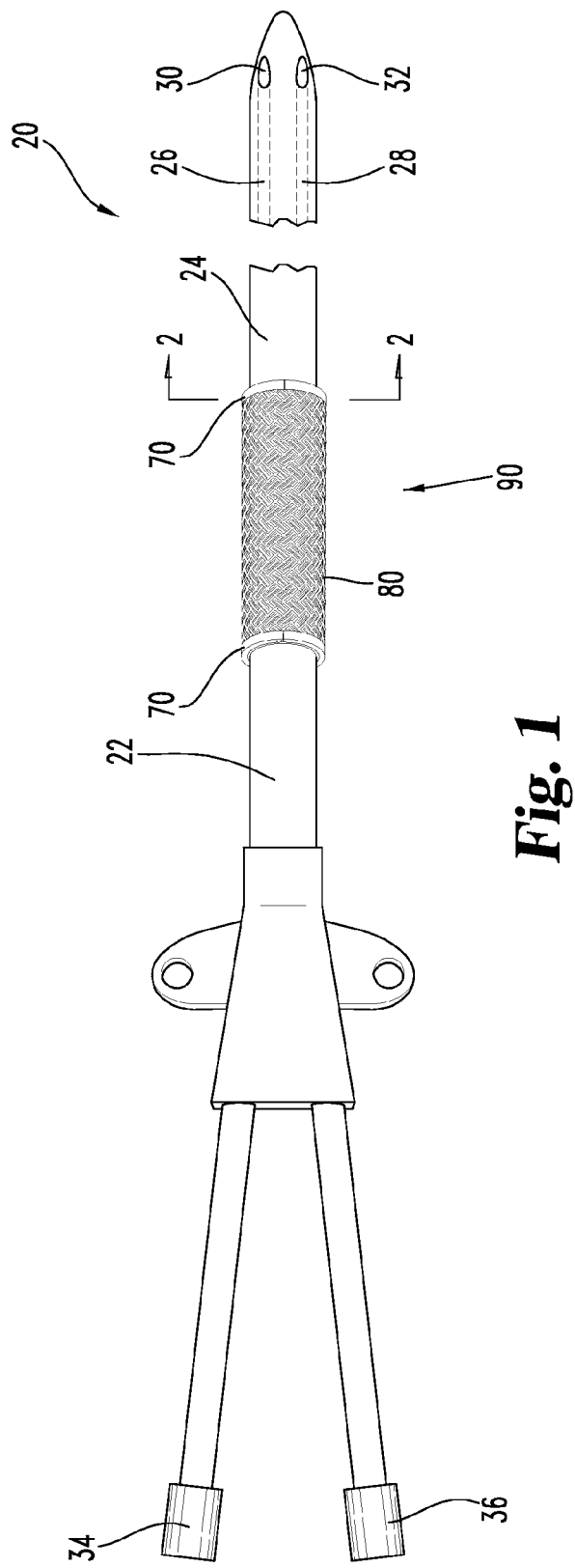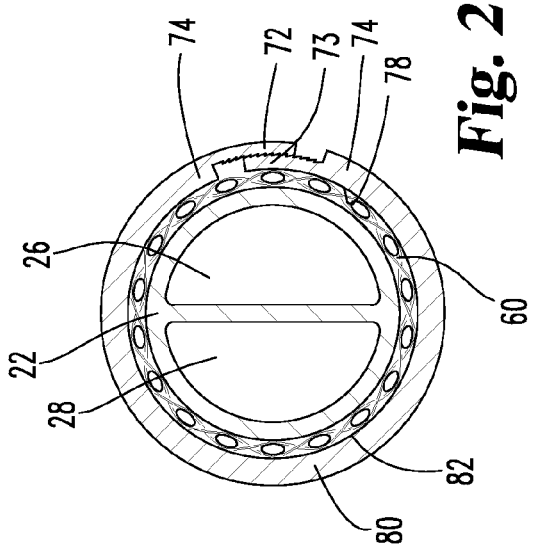

MOVEABLE CUFF

CROSS REFERENCE TO RELATED APPLICATIONS

The present application claims the benefit of U.S. Provisional Patent Application Ser. No. 61/786,929 filed Mar. 15, 2013, which is hereby incorporated by reference.

BACKGROUND

This disclosure relates to catheter cuffs, and more specifically to catheter cuffs whose position can be relocated by an operator.

Many types of catheters are indicated for short or long term access into a body. In the context of human medicine this includes monitoring of internal pressure, e.g., pulmonary blood pressure, blood sampling, nutrition and administration of drugs and fluids.

One type of catheter that is used for long term access is a tunneled catheter that passes through a length of subcutaneous tissue prior to entering the site to which access is desired, e.g., a blood vessel. This can be done by first gaining access to the desired site e.g., the internal jugular vein or subclavian vein, through the skin. A second incision site through the skin is then created spaced apart from the first access site. The catheter is then tunneled through the subcutaneous tissue between the first and second incision sites and is inserted into the previously-accessed desired site in the body. This locates the external portion of the catheter away from the first access site, perhaps to a location more convenient or otherwise preferable for the patient or physician.

In some cases, the catheter includes a tissue ingrowth body on the external surface of the catheter to promote subcutaneous tissue to incorporate around the ingrowth body to fix the catheter in place and to block pathogens from migrating along the length of the catheter into the body. For example, a fiber cuff can be glued to the catheter shaft 1 cm to 13 cm away from the catheter manifold.

Permanently gluing the cuff in place on the catheter during manufacture limits the uses an individual catheter can be used for and places limitation on the use of the catheter as the length of tunneling will be dictated by the amount of catheter remaining after placement in the desired site in the body, and a physician cannot always accurately predicte how much catheter length will be required to reach a desired location. Once properly located, the physician will not want to move the tip of the catheter, and a physician will not want to change out an inserted catheter with a new catheter with a different cuff location to accommodate tunneling.

SUMMARY

Disclosed is a catheter assembly that includes a catheter and a movable cuff assembly engaged on the external surface of the catheter. The movable cuff assembly includes a sleeve, a tissue ingrowth cuff affixed to the sleeve and a clamp affixed to the sleeve, where engaging the clamp substantially fixes the cuff assembly in position on the catheter but when the clamp is not engaged, the cuff assembly is slidably movable over the external surface of the catheter.

The disclosed catheter may be substantially smooth and free of projections. The disclosed sleeve may define a plurality of openings with the tissue ingrowth cuff interwoven in the openings. The disclosed catheter and sleeve may have similar pliability. The disclosed clamp may include a living hinge. Engaging the disclosed clamp may reduce the inner diameter of the cuff assembly below the outer diameter of the catheter. The disclosed cuff assembly my include a second clamp affixed to the sleeve. The disclosed catheter assembly may be used as part of a kit.

BRIEF DESCRIPTION OF THE DRAWINGS

FIG. 1 illustrates a perspective view of a catheter assembly including a catheter, and a cuff assembly on the catheter.

FIG. 2 illustrates a cross-section of FIG. 1 along line 2-2.

DETAILED DESCRIPTION

Figure 3:
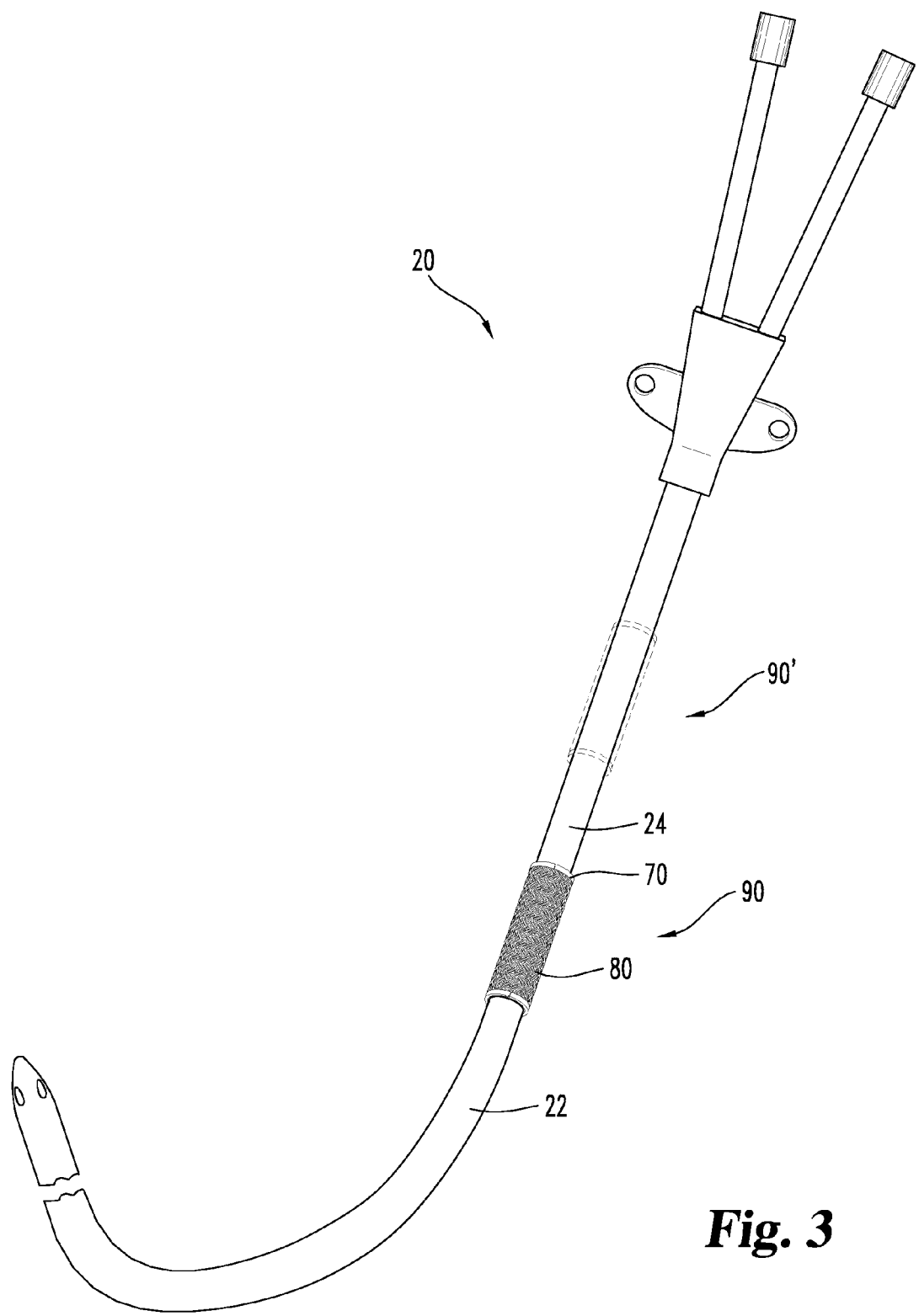
FIG. 3 illustrates a perspective view of the FIG. 1 catheter assembly showing longitudinal movement of the tissue ingrowth cuff along the long axis of the catheter.

Reference will now be made to certain embodiments and specific language will be used to describe the same. It should be understood that no limitation of the scope of this disclosure and the claims are thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

The disclosed positioning system features a catheter assembly that includes a catheter with an external surface and an outer diameter, a movable cuff assembly engaged around the circumference of the catheter, where the movable cuff assembly includes a sleeve, a tissue ingrowth cuff affixed to the sleeve, and a clamp affixed to the sleeve, where when the first clamp is engaged, the movable cuff assembly is substantially fixed in position on the external surface of the catheter and wherein when the first clamp is disengaged, the movable cuff assembly is slidably movable over the external surface of the catheter. The disclosed system allows for placement of the cuff at a position along the catheter after insertion of the catheter into the body of a patient; the operator does not need to pre-determine where the cuff is to be located prior to surgery.

As contemplated herein, embodiments of the disclosed system can include a cuff positioning system useful in conjunction with a thin-walled catheter, a dialysis catheter, a high-flow catheter, a high pressure catheter, or a tunneled central catheter as non-limiting examples. The skilled artisan will recognize that the disclosed system can be used with other types of catheters in addition to those listed above.

Catheters such as thin-walled catheters, high-flow catheters, and high pressure catheters generally include at least one lumen usable to pass fluids into or out of a patient's body. The disclosed system should not be understood to be limited to the number of lumens present in the catheter. Catheters with different numbers of lumens are used for different purposes, as is known to the skilled artisan. Moreover, embodiments of the disclosed system may include other lumen configurations and cross sections, such as multiple lumens of different sizes and shapes. Furthermore, the disclosed system may also be used with catheters that have no lumen.

Referring to the drawings, FIGS. 1 and 2 illustrate a particular embodiment of catheter assembly 20. Catheter assembly 20 includes catheter 22, sleeve 60, clamp 70 and cuff 80. Catheter 22 has external surface 24 and defines lumen 26, lumen 28, port 30 and port 32. The embodiment of catheter 22 also includes connectors 34 and 36. Connector 34 is fluidly connected to port 30 via lumen 26. Connector 36 is fluidly connected to port 32 via lumen 28. Connectors 34 and 36 may be luer lock fasteners configured to connect external tubing to catheter 22. However, connectors 34 and 36 may be any type of appropriate connector, including non-fluid connections where appropriate. For example, an optical connection may be used in conjunction with an optical sensor. External surface 24 may be substantially smooth and free of projections.

Figure 4:
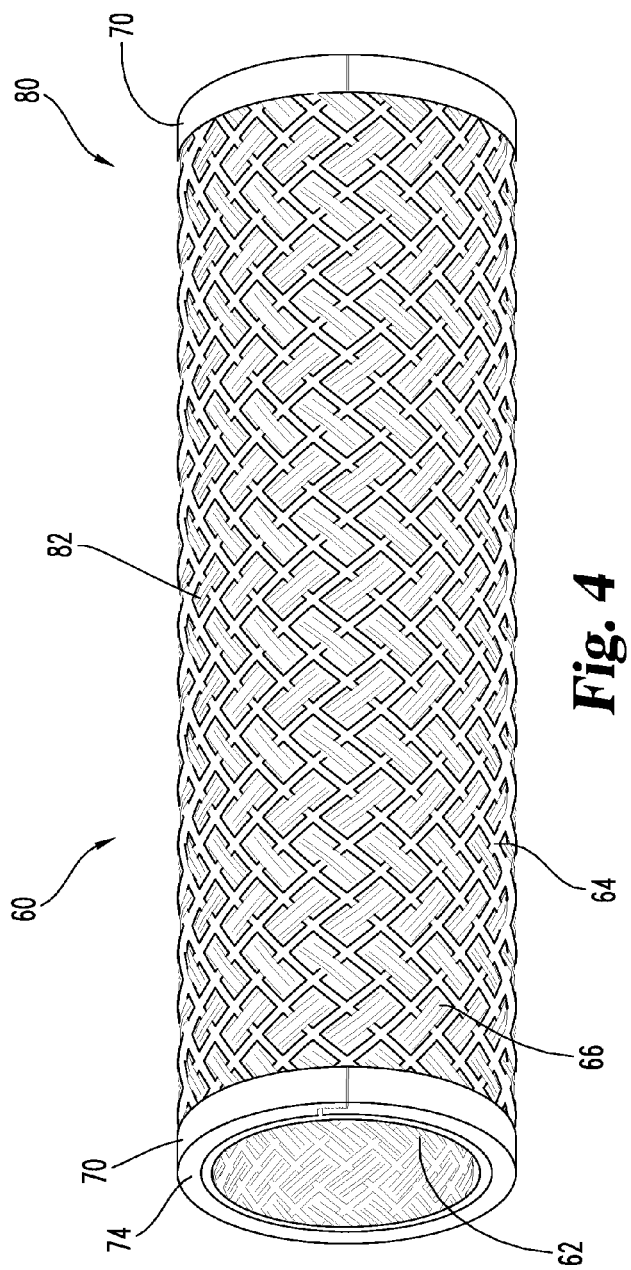
FIG. 4 illustrates a perspective view of the FIG. 1 cuff assembly.
Figure 5:
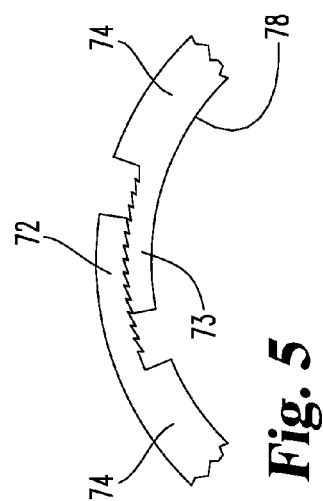
FIG. 5 illustrates a side elevational view of a clamp portion of the FIG. 4 cuff assembly.

Referring to FIGS. 4 and 5, embodiments of sleeve 60, clamps 70 and cuff 80 are illustrated in closer detail. Sleeve 60 defines lumen 62. Sleeve 60 includes mesh 64 that defines a plurality of openings 66 in sleeve 60. Sleeve 60 may be a cylindrical mesh of nitinol or other bio-compatible material. Sleeve 60 and catheter 22 may have similar pliability.

Clamps 70 are affixed to the ends of sleeve 60. The illustrated example of a clamp 70 includes mating locking elements 72 and 73 that are constructed and arranged to permit a one-way ratcheting connection that allows the internal diameter of clamps 70 to be incrementally reduced to clamp around external surface 24 to substantially grip external surface 24. Clamps 70 may be constructed and arranged on sleeve 60 such that the inner diameter of cuff assembly 90 (at least the portion positioned under clamps 70) may be made smaller than the external diameter of catheter 22 by engaging clamps 70.

Cuff 80 in this example includes fibers 82 that are interwoven around mesh 64 through openings 66. Fibers 82 are constructed of a biocompatible material that promotes tissue-ingrowth. Cuff 80 mirrors the cylindrical shape of sleeve 60. Cuff 80 is a cylindrically shaped cuff of tissue-ingrowth material that promotes ingrowth of tissue when implanted in bodily tissue, such as under a patient's skin. Sleeve 60 with cuff 80 interwoven in mesh 64 and clamps 70 define cuff assembly 90.

Catheter assembly 20 is assembled by inserting catheter 22 in lumen 62 of sleeve 60. The internal surface of cuff assembly 90 and external surface 24 are constructed and arranged such that cuff assembly 90 is longitudinally slidable along the long axis of catheter 22 (as long as clamp 70 is not tightened or otherwise engaged to reduce the diameter of clamp 70). Cuff assembly 90 may be moved along the length of catheter 22 over external surface 24. As shown in FIG. 3, cuff assembly 90 may be repositioned from position X to position X', or vice versa.

Clamps 70 may be engaged to substantially fix cuff assembly 90 in position on catheter 22. The diameter of clamps 70 may be incrementally decreased through ratcheting movement facilitated by moving one or both locking elements 72 and 73 with respect to each other until clamps 70 grip external surface 24 of catheter 22 to substantially limit cuff assembly 90 from sliding along catheter 22. In this way, cuff assembly 90 can be located in a particular position on catheter 22 after catheter 22 has been inserted into a patient and a particular position for cuff assembly 90 can be determined based on a particular patient's anatomy and the actual position of catheter 22 when inserted into the patient. Once clamps 70 are engaged, cuff assembly 90 is substantially fixed in position on catheter 22.

Figure 6:
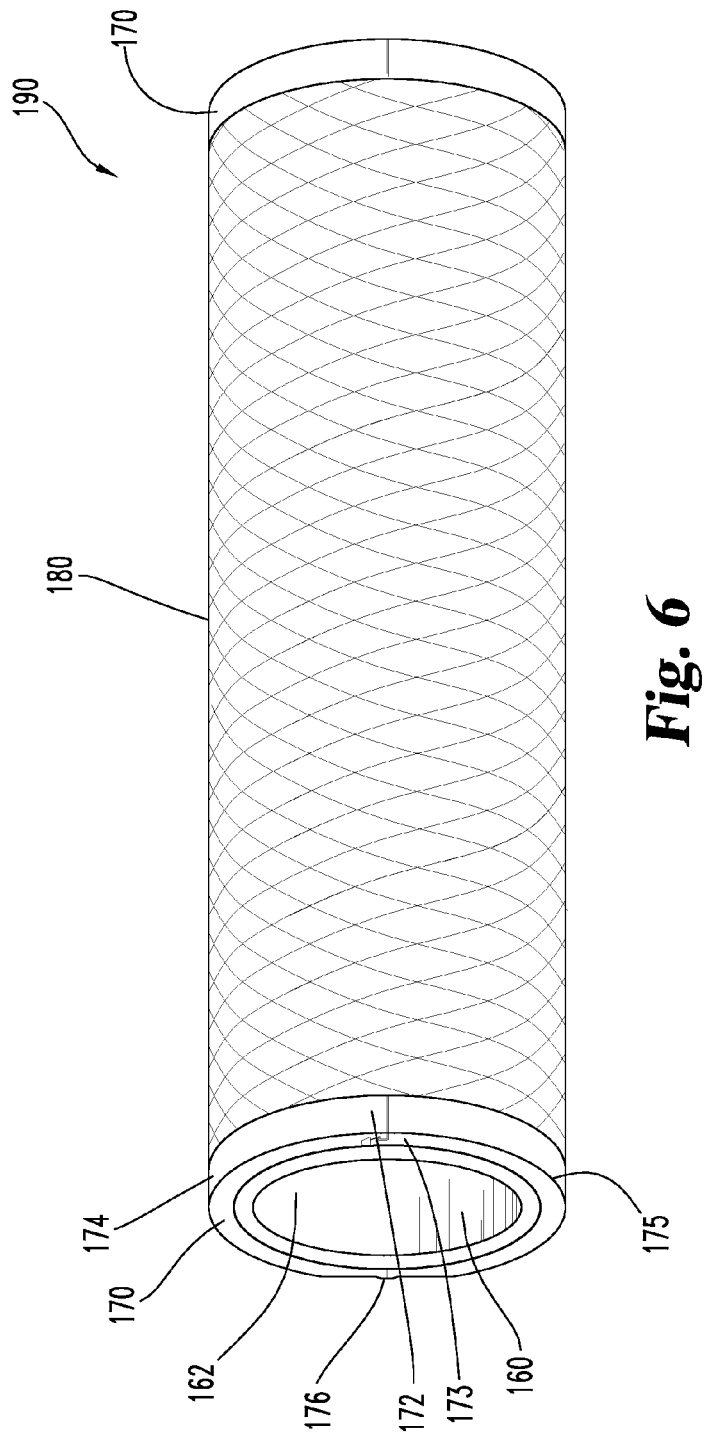
FIG. 6 illustrates an alternative cuff assembly.
Figure 7:
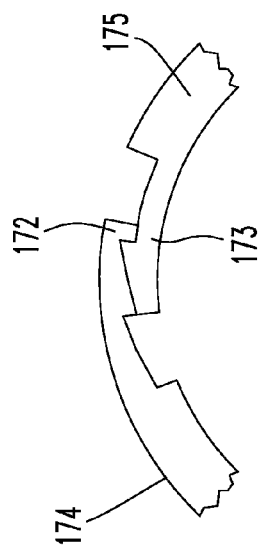
FIG. 7 illustrates a side elevational view of a clamp portion of the FIG. 6 cuff assembly.

FIGS. 6 and 7 illustrate cuff assembly 190, an alternate embodiment of cuff assembly 90. Cuff assembly 190 includes sleeve 160, clamps 170 and cuff 180. Sleeve 160 is a tubular sleeve that defines lumen 162 that is large enough to allow catheter 22 to pass through lumen 162.

Clamps 170 are affixed to the ends of sleeve 160. Clamps 170 include bodies 174 and 175 attached at hinge 176. Hinge 176 may be a living hinge. Body 174 includes locking element 172 and body 175 includes locking element 173. Locking element 172 and 173 are constructed and arranged to permit a one-way tightening connection that allows the internal diameter of clamps 70 to be reduced to clamp around external surface 24 to substantially grip external surface 24. Compared to locking elements 72 and 73, locking elements 172 and 173 include a smaller number of teeth-like structures that ratchets only upon comparatively larger movements. For example, as indicated in FIG. 7 elements 172 and 173 may have a single relative pair of locking surfaces or features, so that clamps 170 have an unlocked configuration allowing movement of assembly 190 (e.g. FIG. 7) and a locked configuration to hold assembly 190 with respect to catheter 22. The locked configuration occurs when one or both of bodies 174 and 175 are moved with respect to each other (e.g. body 175 counterclockwise and/or body 174 clockwise as seen in FIG. 7) and elements 172 and 173 slip over each other to the locking engagement.

Cuff 180 is a cylindrically shaped tissue-ingrowth cuff attached around the circumference of sleeve 160, for example, by an adhesive (not illustrated). Cuff 180 is constructed from a biocompatible material that promotes ingrowth of tissue when implanted in bodily tissue, such as under a patient's skin.

Cuff assembly 190 otherwise functions in the same way described above with regard to cuff assembly 90. It will be understood that catheter assembly 20, 120 or parts thereof as described previously may be provided as part of a kit for a surgeon or other medical professional. Such a kit may include, for example, a catheter, a sleeve, and a tissue ingrowth cuff in any of the embodiments noted above. A kit may also include additional tools (e.g. introducer(s) or needle(s)) useful for inserting or using assembly 20.

This disclosure serves to illustrate and describe what is claimed below to aid in the interpretation of the claims. However, this disclosure is not restrictive in character because not every embodiment covered by the claims is necessarily illustrated and described. All changes and modifications that come within the scope of the claims are desired to be protected, not just those embodiments explicitly described.

I claim:

1. A catheter assembly comprising:
    a catheter having an external surface having an outer diameter;
    a movable cuff assembly engaged around the circumference of the catheter, the movable cuff assembly comprising:
        a sleeve that defines a plurality of openings;
        a tissue ingrowth cuff woven in the plurality of openings and affixed to the sleeve; and
        a first engagable clamp affixed to the sleeve, wherein when the first clamp is engaged, the movable cuff assembly is substantially fixed in position on the external surface of the catheter and wherein when the first clamp is disengaged, the movable cuff assembly is slidably movable over the external surface of the catheter.

2. The catheter assembly of claim 1, wherein the external surface of the catheter is substantially smooth and free of projections.

3. The catheter assembly of claim 1, wherein the sleeve and the catheter have similar pliability.

4. The catheter assembly of claim 1, wherein the first engageable clamp further comprises a first living hinge.

5. The catheter assembly of claim 1, wherein the movable cuff assembly has an inner diameter larger than the outer diameter of the catheter when the first clamp is disengaged and wherein the inner diameter of the movable cuff assembly is smaller than the outer diameter of the catheter when the first clamp is engaged.

6. The catheter assembly of claim 1, further comprising a second engagable clamp affixed to the sleeve, wherein when the second engagable clamp is engaged, the movable cuff assembly is substantially fixed in position on the external surface of the catheter.

7. The catheter assembly of claim 6, wherein the movable cuff assembly has an inner diameter larger than the outer diameter of the catheter when the second clamp is disengaged and wherein the inner diameter of the movable cuff assembly is smaller than the outer diameter of the catheter when the second clamp is engaged.

8. The catheter assembly of claim 6, wherein the second engageable clamp further comprises a second living hinge.

9. A kit comprising:
- a catheter including an external surface and having an outer diameter;
- a movable cuff assembly engagable around the circumference of the catheter, the movable cuff assembly comprising:
  - a sleeve that defines a plurality of openings;
  - a tissue ingrowth cuff woven in the plurality of openings and affixed to the sleeve; and
  - a first engagable clamp affixed to the sleeve, wherein when the first clamp is engaged, the movable cuff assembly is substantially fixed in position on the external surface of the catheter and wherein when the first clamp is disengaged, the movable cuff assembly is slidably movable over the external surface of the catheter.

10. The kit of claim 9, wherein the external surface of the catheter is substantially smooth and free of projections.

11. The kit of claim 9, wherein the sleeve and that catheter have similar pliability.

12. The kit of claim 9, wherein the movable cuff assembly has an inner diameter larger than the outer diameter of the catheter when the first clamp is disengaged and wherein the inner diameter of the movable cuff assembly is smaller than the outer diameter of the catheter when the first clamp is engaged.

13. The kit of claim 9, further comprising a second engagable clamp affixed to the sleeve, wherein when the second engagable clamp is engaged, the movable cuff assembly is substantially fixed in position on the external surface of the catheter.

14. The kit of claim 13, wherein the movable cuff assembly has an inner diameter larger than the outer diameter of the catheter when the second clamp is disengaged and wherein the inner diameter of the movable cuff assembly is smaller than the outer diameter of the catheter when the second clamp is engaged.

15. A method of uniting an apparatus, the method comprising:
- for a particular clinical application for a particular patient, determining a longitudinal location on a catheter to position a tissue ingrowth cuff, wherein the catheter has an external surface having an outer diameter;
- moving a movable cuff assembly longitudinally along the catheter, wherein the movable cuff assembly is positioned around the catheter, wherein the movable cuff assembly includes a sleeve that defines a plurality of openings, a tissue ingrowth cuff woven in the plurality of openings and affixed to the sleeve and a first engagable clamp affixed to the sleeve, wherein when the first clamp is engaged, the movable cuff assembly is substantially fixed in position on the external surface of the catheter and wherein when the first clamp is disengaged, the movable cuff assembly is slidably movable over the external surface of the catheter; and
- engaging the first clamp thereby longitudinally positioning the movable cuff assembly on the catheter.

16. The method of claim 15, further comprising:
- before determining a longitudinal location on the catheter to locate the movable cuff assembly, inserting the catheter into the particular patient.

17. The method of claim 15, wherein the external surface of the catheter is substantially smooth and free of projections.

18. The method of claim 15, wherein the movable cuff assembly has an inner diameter larger than the outer diameter of the catheter when the first clamp is disengaged and wherein the inner diameter of the movable cuff assembly is smaller than the outer diameter of the catheter when the first clamp is engaged.

* * * * *